(12) United States Patent
Liu et al.

(10) Patent No.: US 7,638,338 B2
(45) Date of Patent: Dec. 29, 2009

(54) MEASUREMENT AND CALIBRATION METHOD FOR SAMPLE INJECTION VOLUME AND MOBILE PHASE DELIVERY RATE IN A ULTRA MICRO-SCALE LIQUID PHASE DELIVERY SYSTEM

(75) Inventors: Kung-Tien Liu, Lung-Tan (TW);
Jyh-Perng Chiu, Lung-Tan (TW);
Hsuan-Erh Chao, Lung-Tan (TW);
Ying-Kai Fu, Lung-Tan (TW)

(73) Assignee: Atomic Energy Council - Institute of Nuclear Energy Research, Taiwan (CN)

( * ) Notice: Subject to any disclaimer, the term of this patent is extended or adjusted under 35 U.S.C. 154(b) by 969 days.

(21) Appl. No.: 11/119,215

(22) Filed: Apr. 29, 2005

(65) Prior Publication Data
US 2006/0051242 A1    Mar. 9, 2006

(30) Foreign Application Priority Data
Sep. 9, 2004    (TW) .............................. 93127319 A

(51) Int. Cl.
*G01N 33/00* (2006.01)
(52) U.S. Cl. ..................... 436/56; 422/68.1; 422/73; 422/99
(58) Field of Classification Search ................. 436/56; 422/68.1, 73, 99
See application file for complete search history.

(56) References Cited
OTHER PUBLICATIONS
None*
* cited by examiner

*Primary Examiner*—Sam P Siefke
(74) *Attorney, Agent, or Firm*—Ladas & Parry LLP

(57) ABSTRACT

The present invention provides a method for measuring and calibrating sample injection volume or mobile phase delivery rate of any type of micropumps or their integrated systems by using the direct proportion of the total activity (or mass) to the delivery rate (or volume) of a radiochemical nuclide with known activity in a certain time period. Also, the present invention may adjust the range of measurement and calibration from micro-liter (μL) to pico-liter (pL) or from μL/min to pL/min by selecting nuclide species and their concentrations from different liquid calibration radiation sources.

20 Claims, 5 Drawing Sheets

(a)

(b)

(c)

MEASUREMENT AND CALIBRATION METHOD FOR SAMPLE INJECTION VOLUME AND MOBILE PHASE DELIVERY RATE IN A ULTRA MICRO-SCALE LIQUID PHASE DELIVERY SYSTEM

BACKGROUND OF THE INVENTION

1. Field of the Invention

The present invention relates to a method for measuring and calibrating sample injection volume and mobile phase delivery rate in a ultra micro-scale liquid phase delivery system, particularly a method using radiochemical substances and radiochemical analytical techniques to make the range of measurement or calibration achieve micro-volume or micro-flow rate grades.

2. Description of the Prior Art

Ultra micro-scale liquid phase delivery technology is the main trend and the key technology of development and application in the biomedicine, clinical diagnosis, drug screening, nano science and technology, and analytical technique currently and in the future, with its scope covering, for example, micro-liquid chromatography (μ-LC), capillary liquid chromatography, liquid chromatography mass spectrometer (LCMS), microdialysis (MD), lab-on-a-chip or microfluidic biochip, microarray biochip, micro total analysis system (μ-TAS), micro flow injection analysis (μ-FIA) or chip arrayer etc. Components such as μ-LC pump, capillary LC pump, syringe pump, micro driven spray and dipper must be used as delivery tools for samples and mobile phases.

As for the current, more mature ultra micro-scale liquid phase delivery technology, although the effective lower limit of these delivery tools for mobile phase delivery may be about 0.1 μL/min (for example, capillary LC pump) or 0.1 μL/h (for example, syringe pump), and the effective lower limit for sample single injection or spray volume is about 0.01 μL (for example, capillary LC syringe) or 0.1 nL (for example, chip arrayer), there is no convenient, rapid technology or apparatus for the measurement and calibration of mobile phase delivery rate and sample injection or spray volume.

(1) Mobile Phase Delivery Rate

The technologies known for measuring the flow rate of a fluid system include mechanical turbine, pressure difference (pneumotachometer), thermal sensitive, electromagnetic or ultrasonic technologies etc., with a measuring range from L/s to mL/min. However, the measuring methods mentioned above are not applicable for measuring the flow rate in an ultra micro-scale fluid system. For example, in Jian-zhong Fu et al., "the Architecture of a Novel Thermal Pulse Microflowmeter" (Patent No. TW 384,392), the fundamental principle is to allow the fluid to be measured flow through a micro channel, and to set a heater in the upstream of the micro channel for heating, then to set several thermal sensor modules in the downstream of the micro channel to sense the heated fluid, then to calculate the time difference and then to make it divided by the product of cross-sectional area of the micro channel and the distance between the two points. Although the principle of the invention is quite simple, the difficultly lies in that if the resolution of the flow rate measurement needs to be increased, the measured time difference will be increased or the distance between the thermal sensor modules will be decreased. Therefore, the measured time difference and the layout of thermal sensor modules in the invention will be confined by space. In addition, according to the data disclosed in the invention by Jian-zhong Fu et al., the flow range will drop from 5475 sccm to 608 sccm when the measuring time ranges from 0.1 mS to 0.9 mS. The reference also discloses that accurate time control, including suitable reaction time of temperature transmission (heat balance time) being required to be less than 0.1 mS, is a key technology which is difficult to meet by using the layout.

"Pneumotachometer" invented by Ying-song Xu (Patent No. TW 483,526), which contains a torpedo sinker type sinking flow meter having induction components which may convert pressure differences between the front-end pitot hole (over against the flowage direction of the fluid) and the static vents (multiple surrounding the surface of the torpedo sinker, in symmetrical distribution) to electronic signal, is put into a moving fluid by a sling to measure the flow rate of the fluid. The difficulty lies in that the bulk of the design is too large, and thus is not suitable for the operation of being placed directly into a micro channel which has an inner diameter between several mm to several μm.

"A Method for Setting Flow Coefficients and the Flow Measuring apparatus Using the method" (Patent No. TW 407,197) invented by Kouji Kennsan provides mainly a method for setting flow coefficients by establishing the functional relation between the flow coefficients and the flow rate. It also discloses the concept of an apparatus which may be used for setting flow coefficients and measuring the flow rate of a thermal flow sensor and an ultrasonic flowmeter in the patent. However, according to the functional relation between flow coefficients and flow rates disclosed in the invention by Kouji Kennsan (as shown in FIGS. 4-7 and FIGS. 10-19 of the specification), the ranges of flow rates are all up to meter/second with sensor parts being relatively larger. Therefore, the design is not applicable for an ultra micro-scale flow system.

In "Ultrasonic Flowmeter" (Patent No. TW 523,580) invented by Imaigu and Takataaki, the flow rate of a fluid is measured by the differences between the ultrasonic transmission times when the liquid flows through the two measurement units on a measuring tube. However, the difficulty of the design lies in that the measuring process is easily disturbed by perturbation, thereby increasing the uncertainty. In addition, factors such as large parts also make the design inapplicable for an ultra micro-scale flow system.

As compared with the known methods mentioned above, an optical fluid flowmeter system is relatively applicable for measuring the flow rate of a micro-scale system. Common fluid measurement methods include particle image velocimetry (PIV) and laser doppler velocimetry (LDV). PIV is a technology for measuring flow rates by an optical method. In experiments, some small particles are added into a flowing medium and the distances between the small particles are recorded by a secondary photography and then divided by the time intervals of the secondary photography to calculate the flow rate of the medium. The advantages of PIV include simple principle, easy-to-process data, high accuracy and measuring range up to below μL/min. However, its disadvantages include the uncertainty of measurement due to the differences between the flow rate at the center and that of the tube wall when the fluid moves in the micro channel in the mode of laminar flow, and a measurement deviation that is difficult to be calibrated when perturbation and eddy of flow arise in the micro channel. The measurement uncertainty and deviation will increase with the decrease of the tube diameter of the micro channel and the increase of the flow rates. In addition, PIV technology for measuring the micro diameter scope is known as μPIV, wherein a pulse type Nd: YAG laser light source must be used to create enough rapid and high brightness exposure to avoid blurring caused by rapid moving particles. However, the disadvantage of the method is that a microscope digital photographic equipment must be used. Therefore, there are difficulties in microscope focusing, injection and control of micron particles in experiment. A complicated and expensive pulse type equipment of Nd:YAG laser light source is also one of the deficiencies. The principle of LDV is that the wavelength of a reflected light is measured after the delivery of a monochromatic light laser wave. According to the Doppler principle, the wavelength variance of reflected lights is a function of relative moving rate of an object. Therefore, the moving rate of the object can be calculated by the wavelength variance of reflected lights. Although the measuring scope of flow rates by LDV may be between mL/min and μL/min, the disadvantage lies in that equipments of monochromatic light Helium-Neon laser or argon ion laser system used in experiments are significantly complicated and expensive. Furthermore, the uncertainty and deviation in laser wavelength measurement may be increased due to absorption and dispersion by the fluid medium. Occasionally, a high reflective efficiency substance, such as a small particle reflecting bead, must be added to increase the detection sensibility, and meanwhile there are problems such as perturbation and eddy occurring.

(2) Sample Injection Volume

As for the measurement of micro-scale sample injection volume, the most common method is to measure the mass and then convert the result using the density. However, the resolution of a mass measurement method may range from only a mg to μg grade at most, so it is not applicable for measuring the volume of a sample below a μg grade. In addition, in the conventional art, fluorescent materials or dyes are added into a fluid and then the fluorescent absorbance of the fluid is measured and converted into fluid volume. Although significant micro-scale volume may be measured in this way, such as nL, fluorescent materials and dyes have different chemical properties in different fluid media. Therefore, there may be uncertainty and deviation of measurement due to drift of absorption wavelength or quench of absorption strength.

Currently, there is no method or technology for measuring micro-volume and micro-flow rate by radiochemical substances and radiochemical analytical apparatus in any country in the world. However, the method disclosed in the invention for measurement and calibration of radiochemical substances may effectively address the above-mentioned problems. It not only may adjust the range of measurement and calibration from μL to pL or from μL/min to pL/min, but also is applicable for measurement and calibration of sample injection volume, spray volume, dipper adhesive volume and delivery rate of mobile phase. Thus, the invention can effectively address difficulties of prior arts and is expected to have significant influences on the development of the biomedicine, clinical diagnosis, drug screening, nano science and technology and analytical technique in every country in the future.

SUMMARY OF THE INVENTION

The object of the invention is to provide a method for measuring sample injection volume and mobile phase delivery rate of an ultra micro-scale liquid phase delivery system, in which radiochemical substances and radiochemical analytical techniques are used to make the measurement range achieve the micro-volume and micro-flow rate grade.

Another object of the invention is to provide a method for measuring and calibrating sample injection volume and mobile phase delivery rate of an ultra micro-scale liquid phase delivery system, in which radiochemical substances and radiochemical analytical techniques are used to make the range of measurement and calibration achieve the micro-volume or micro-flow rate grade.

Still another object of the invention is to provide a method for adjusting the range of measurement and calibration from micro-liter (μL) to pico-liter (pL) or from μL/min to pL/min by selecting various nuclides and their concentrations of different liquid standard sources.

Figure 1:
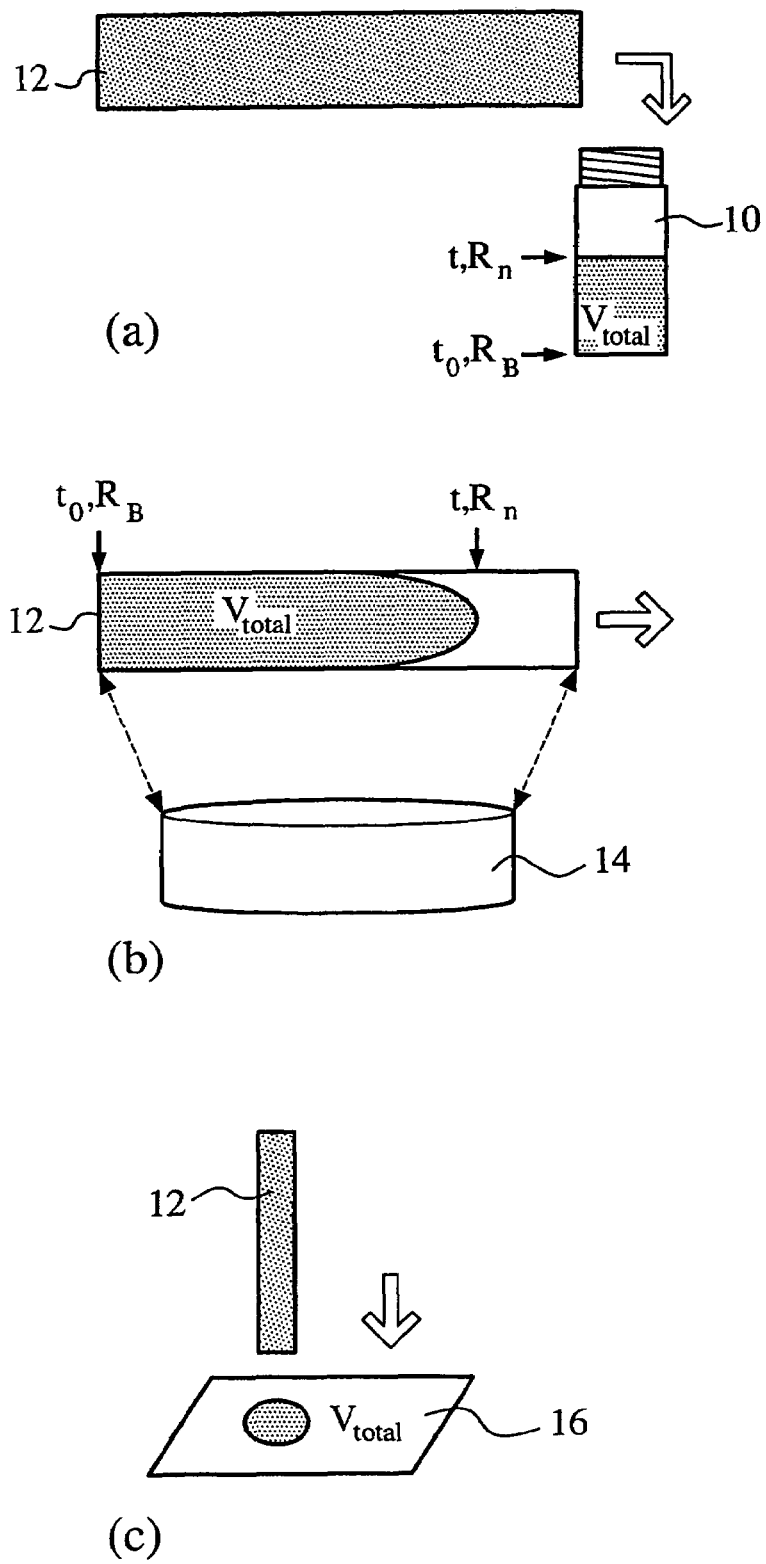
FIG. 1 is a schematic view of the three modes for measurement and calibration of micro-scale volume and flow rate in the present invention, i.e., (a) fractional collection, (b) stop-flow and (c) quantitative spray.

DETAILED DESCRIPTION OF THE INVENTION (1) Fundamental Principle

To rapidly measure and calibrate sample injection volume or mobile phase delivery rate of micropumps or their integrated systems, it is based on the direct proportion of the total activity (or counting rate or mass) to delivery rate (or volume) of a radiochemical nuclide with known activity in a certain time period.

(2) Selection of Standards

Because the ranges of measurement and calibration (for example, from μL to pL in volume or from μL/min to pL/min in flow rate) are different, various nuclides species (for example, the ion state or a complex form) and concentrations (for example, different dilution folds) of different liquid state (for example, hydrophilic or hydrophobic) calibration sources must be selected as usable standards for measurement and calibration, and the liquid state standards for measurement may be adjusted to a water solution system. Standards are selected according to factors such as half-life period of nuclides, specific activity (TBq/g), atomic mass (amu) and mode of decay. In addition, availability of standards shall also be considered. The data of some alternative nuclides is listed in Table 1.

TABLE 1

Data of Nuclides

| Nuclide | Half-life Period | Specific Activity (TBq/g) | Atomic Mass (amu) | Mode of Decay |
|---------|------------------|---------------------------|-------------------|---------------|
| Co-57   | 272.11 d         | 310                       | 56.9363           | EC to Fe-57   |
| Co-60   | 1925.12 d        | 42                        | 59.9338           | β- to Ni-60   |
| Cs-137  | 11015 d          | 3.2                       | 136.9071          | β- to Ba-137  |
| Eu-152  | 4945.5 d         | 6.5                       | 151.9217          | EC to Sm-152  |
|         |                  |                           |                   | β- to Gd-152  |

TABLE 1-continued

Data of Nuclides

| Nuclide | Half-life Period | Specific Activity (TBq/g) | Atomic Mass (amu) | Mode of Decay |
|---------|------------------|---------------------------|-------------------|---------------|
| Ga-67   | 3.26154 d        | 22000                     | 66.9282           | EC to Zn-67   |
| I-125   | 59.408 d         | 640                       | 124.9046          | EC to Te-125  |
| I-131   | 8.0197 d         | 4600                      | 130.9061          | β- to Xe-131, γ |
| In-111  | 2.80477 d        | 15000                     | 110.9051          | EC to Cd-111  |
| Mo-99   | 65.94 h          | 18000                     | 98.9077           | β- to Tc-99   |
| P-32    | 14.262 d         | 11000                     | 31.9739           | β- to S-32    |
| Sm-153  | 46.284 h         | 16000                     | 152.9221          | β- to Eu-153  |
| Tc-99m  | 6.00718 h        | 190000                    | 98.9063           | IT to Tc-99   |
| TI-201  | 3.0456 d         | 7900                      | 200.9708          | EC to Hg-201  |

(3) The Range of Measurement and Calibration

The range of measurement or calibration may be adjusted from micro-liter (μL) to pico-liter (pL) or from μL/min to pL/min by selecting various nuclides and their concentrations of different liquid standard sources.

(4) Measuring Mode for Sample Injection Volume and Mobile Phase Delivery Rate

The present invention may be carried out in three modes: fractional collection, stop-flow and quantitative spray, as shown in FIGS. 1(a), 1(b) and 1(c), respectively. Further details are illustrated as follows:

(a) Fractional collection mode: A radiochemical analytical apparatus (for example, a MCA gamma spectrometer, a gas proportional counter, a dose calibrator or an ion chamber) is used directly for counting after the collection of the source solution 12 for a time period of t by the vial 10; or a radioactivity counting apparatus (for example, a liquid scintillation analyzer) is used for counting after the mixing of the source solution 12 with cocktail scintillator in advance. The resulted counting rate is modified by the half-life period calibration to be $R_n$ and the empty vial counting rate $R_B$ may be taken as a background value at $t_0$, and both may be substituted into Formula 9 and Formula 11 (as described below) to calculate volume and flow rate of a delivery source.

(b) Stop-flow mode: With an appropriate shielding (for example, lead shielding), $R_B$ at $t_0$ can be near the background value. The total activity of the radiochemical source solution 12 in the loop is directly measured by the radioactivity counting apparatus 14 (for example, a MCA gamma spectrometer, a gas proportional counter, a dose calibrator or an ion chamber etc.) when the flow time is t and the pump is stopped; or the total activity in the loop is measured by the radiochemical analytical apparatus (for example, a liquid scintillation analyzer) after the cocktail scintillator is mixed with standard source. The resulted counting rate is modified by the half-life period calibration to be $R_n$, which may be substituted into Formula 9 and Formula 11 (as described below) to calculate volume and flow rate of a delivery source.

(c) Quantitative spray: The fundamental principal of this mode is the same as that of the fractional collection mode. Droplets sprayed quantificationally by a sprayer (for example, a thermal spray or piezoelectric driven spray) are collected on a vessel, container or chip 16 and then counted.

Nuclides can be measured directly are those having a gamma decay or electron capture decay property; nuclides should be mixed with a scintillation cocktail and then counted are those without gamma decay or electron capture decay property, such as pure beta decay nuclides Tc-99, H-3 or C-14.

(5) Calibration Modes for Sample Injection Volume and Mobile Phase Delivery Rate When a micropump has delivered a mobile phase or sample at a predetermined flow rate $f_m'$ for a time period t, the predetermined total delivery volume of the resulted standard source is $V_{total}'$, then $$V_{total}' = f_m' \times t, \text{ or} \qquad \text{Formula (1)}$$

$$f_m' = \frac{V_{total}'}{t}. \qquad \text{Formula (2)}$$

The concentration value ($C_n$, mol/g or $C_n'$, Bq/g) of nuclide n standard source is known, thus $$V_{total} = \frac{m_n}{C_n} \qquad \text{Formula (3)}$$

$$= \frac{W_n}{C_n \times M_n}, \qquad \text{Formula (4)}$$

wherein $V_{total}$ is the total actual delivery volume of standard source, $m_n$ is the total mol of nuclide n in $V_{total}$, $W_n$ is the total mass of nuclide n in $V_{total}$, and $M_n$ is the atomic mass (mol/g) of nuclide n.

Substitute $$W_n = \frac{A_n}{Sp_n} \qquad \text{Formual (5)}$$

into Formula (4), then $$V_{total} = \frac{A_n}{C_n \times M_n \times Sp_n}, \qquad \text{Formula (6)}$$

wherein $Sp_n$ is the specific activity value (Bq/g) of nuclide n, which may be obtained from tables, while the activity value $A_n$ (dps) of nuclide n with $W_n$ mass (or $m_n$ mol) must be obtained from experiments, provided that the counting efficiency $Eff_n$ (cps/dps) of nuclide n of an apparatus may be obtained by standard source calibration, then $$Eff_n = \frac{R_n - R_B}{A_n}, \qquad \text{Formula (7)}$$

wherein the background counting rate $R_B$ and the sample counting rate $R_n$ are obtained from actual counting. They are also counting rates when half-time period ($t_{1/2}$) is calibrated to reference time. After the transposition of Formula (7), then:

$$A_n = \frac{R_n - R_B}{Eff_n}. \qquad \text{Formula (8)}$$

The total actual delivery volume $V_{total}$ of standard source may be obtained after Formula (8) is substituted into Formula (6):

$$V_{total} = \frac{R_n - R_B}{C_n \times M_n \times Sp_n \times Eff_n} \quad \text{Formula (9)}$$

$$= k(R_n - R_B), \quad \text{Formula (10)}$$

and the actual flow rate $f_m$ of a mobile phase or sample delivered by pumps may be obtained after Formula (8) is substituted into Formula (2):

$$f_m = \frac{R_n - R_{B_n}}{C_n \times M_n \times Sp_n \times Eff_n \times t} \quad \text{Formula (11)}$$

$$= \frac{k(R_n - R_B)}{t} \quad \text{Formula (12)}$$

$$k = \frac{1}{C_n \times M_n \times Sp_n \times Eff_n} \quad \text{Formula (13)}$$

$$= \frac{1}{C_n' \times Eff_n} \quad \text{Formula (14)}$$

$$k' = \frac{k}{\rho}, \quad \text{Formula (15)}$$

wherein the unit of k is g/cps and the unit of k' is mL/cps.

As for a same nuclide in a solution with same concentration, when the experiment is conducted at the same position by a same measuring apparatus, the sample may be regarded as a point source and deviation resulting from dead time may be neglected due to its tiny volume (μL to pL) and total activity (~Bq). All parameters of denominators in Formula (9) and Formula (11) may be regarded as constants. Therefore, the total actual volume $V_{total}$ of a delivered sample and the actual flow rate $f_m$ of a mobile phase can be obtained by measuring background counting rate $R_B$ and sample counting rate $R_n$.

Standard deviation (σ(R)) of counting rate is:

$$\sigma(R) = \sqrt{\frac{R_n}{t_n} + \frac{R_B}{t_B}}. \quad \text{Formula (16)}$$

Finally, the predetermined volume ($V_{total}'$) and predetermined flow rate ($f_m'$) of the source solution are calibrated by its actual volume ($V_{total}$) and actual flow rate ($f_m$).

$A_n$: nuclide activity, Bq or cps
$C_n$: standard source concentration of nuclide n, mol/g
$C_n'$: standard source concentration of nuclide n, Bq/g
$Eff_n$: counting efficiency of nuclide n
$f_m$: actual flow rate of a mobile phase or sample delivered by pumps, mL/sec
$f_m'$: predetermined flow rate of a mobile phase or sample delivered by pumps, mL/sec
$m_n$: total mol of nuclide n in total volume
$M_n$: atomic mass of nuclide n, g/mol
$R_B$: background counting rate, cps
$R_n$: sample counting rate, cps
$Sp_n$: specific activity of nuclide n, $SP_n=(A_n/W_n)$, Bq/g
t: collection time or delivery time, sec
$t_B$: background counting time
$t_n$: sample (delivery volume) counting time
$V_{total}$: total actual delivery volume of standard source, mL
$V_{total}'$: total predetermined delivery volume of standard source, mL
$W_n$: total mass of nuclide n in total volume
$\rho_n$: density of n standard source solution, g/mL The present invention is further described but not limited by the following embodiments. Without departing from the spirit of the present invention, any variations and modifications by those persons skilled in the art are within the scope of the present invention.

Embodiment 1

Figure 2:
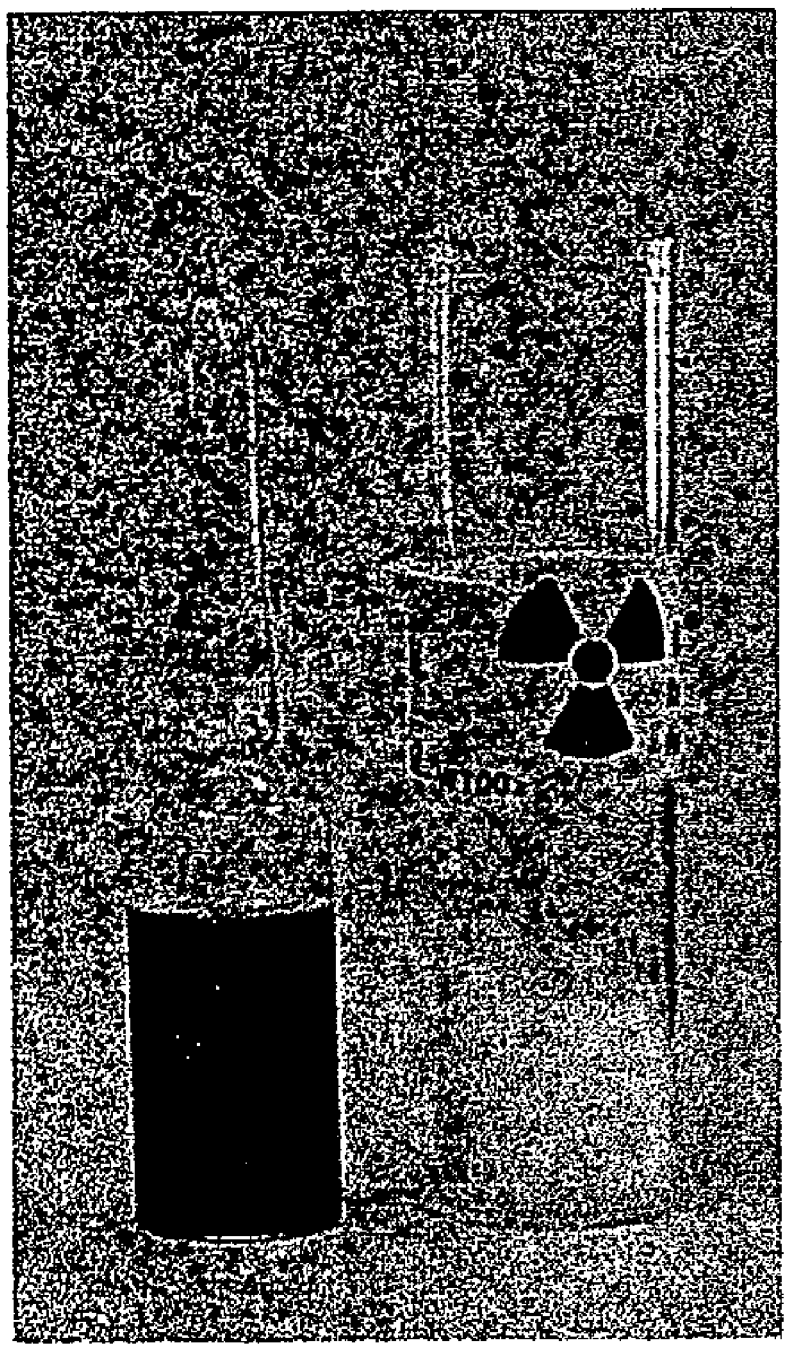
FIG. 2 is a schematic view of the sealed longneck glass bottle containing Cs-137 diluted source solution A in example 1 of the present invention.

(a) Steps for distribution and calibration of Cs-137 source: A 100 μL high strength Cs-137 source with unknown concentration, a 10 μL red dye and a 10 mL de-ionized water are taken into a 15 mL glass bottle. The three ingredients are mixed after the net weights thereof precisely weighed to be known as "Cs-137 diluted source solution A" (hereinafter referred as solution A). 5 mL solution A is taken into a 5 mL longneck glass bottle and the net weight of solution A is precisely weighed. After that, the bottle is sealed by flame. As shown in FIG. 2, the red part is solution A. Activity of solution A is measured by a dose calibrator, and the background value is deducted. Finally, the result is divided by net weight of solution A to measure its concentration (MBq/g).

Figure 3:
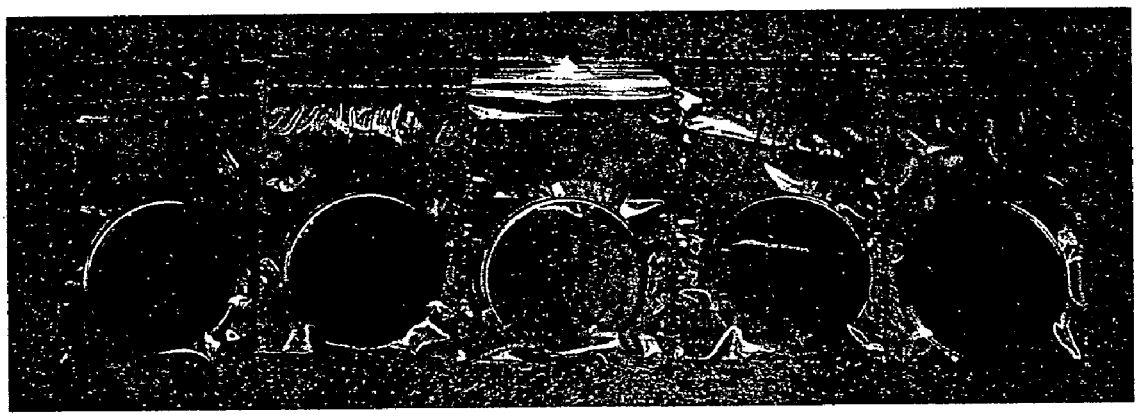
FIG. 3 is a schematic view of the 2-inch stainless plate containing dried Cs-137 diluted source solution A in the measurement and verification test for quantitative spray in example 1 of the present invention.

(b) Steps of the measurement and verification test for quantitative spray: Take 0.5 μL unsealed solution A by a micropipette for five times and drop in five 2-inch stainless plates, respectively. Dry the solution in the plates by an IR lamp and put it into a sealable plastic bag after its net weight is precisely weighed, as shown in FIG. 3. Then, the activities of the steel plates are counted by a MCA gamma spectrometer, and the average value and uncertainty are calculated.

Figure 4:
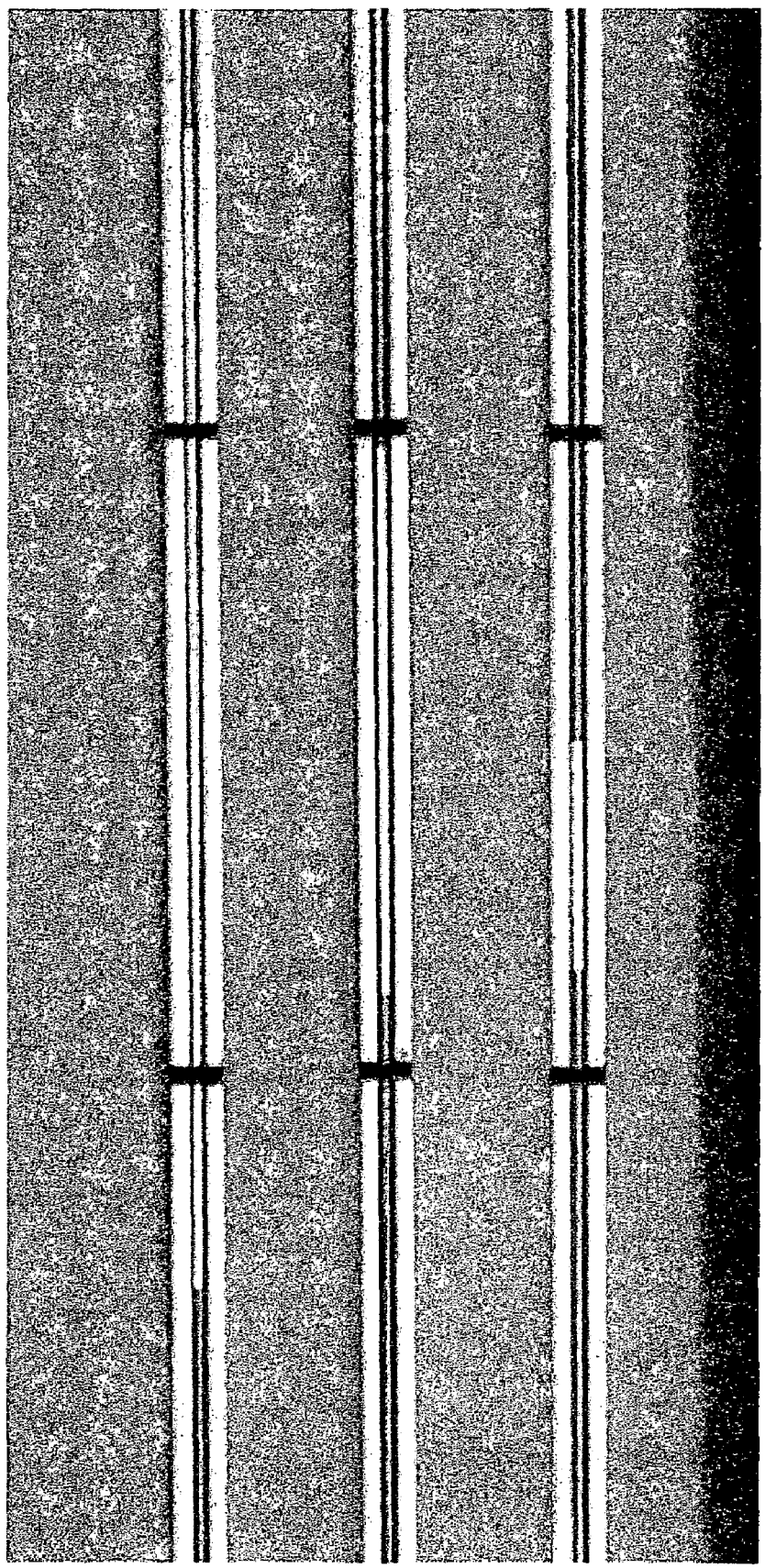
FIG. 4 is a schematic view of the quantitative capillary containing Cs-137 diluted source solution A in the measurement and verification test for stop-flow in example 1 of the present invention.

(c) Steps of the measurement and verification test for stopflow: Suck 0~5 μL unsealed solution A into a quantitative capillary with accurate volume graduation (0~5 μL) and then move the sucked solution to the central part of the capillary. As shown in FIG. 4, the red part is solution A. Then, seal and fix the two ends of the capillary by instant glue. The activity of the capillary is counted by the MCA gamma spectrometer, and the average value and uncertainty are calculated. Since the quantitative capillary is not a point source, the counting geometric factor $k_{geo}$ of the quantitative capillary and the stainless plates must be calibrated.

The results:

(a) Concentration calibration results of solution A, as shown in Table 2 and Table 3:

TABLE 2

| Dilution and Distribution Results of Cs-137 Source | | |
|---|---|---|
| | Volume (mL) | Net Weight (g) |
| Cs-137 source | 0.1 | 0.1004 |
| Red dye | 0.01 | 0.011 |
| De-ionized water | 10 | 9.8782 |
| Total net weight (g) | | 9.9896 |
| Total volume (mL) | 10.11 | |
| Dilution fold | | 99.50 |
| Density (g/mL) | 0.9881 | |

TABLE 3

Concentration Calibration Results of Solution A

|   | Counted Value (MBq) | Net Value (MBq) | Concentration (Bq/g) |
|---|---|---|---|
| 1 | 0.261 | 0.255 | 49203 |
| 2 | 0.260 | 0.254 | 49010 |
| 3 | 0.259 | 0.253 | 48817 |
| 4 | 0.258 | 0.252 | 48624 |
| 5 | 0.259 | 0.253 | 48817 |
| 6 | 0.260 | 0.254 | 49010 |
| 7 | 0.258 | 0.252 | 48624 |
| 8 | 0.257 | 0.251 | 48431 |
| 9 | 0.259 | 0.253 | 48817 |
| 10 | 0.259 | 0.253 | 48817 |
| Average | | | 48817 |
| Standard Deviation | | | 223 |
| Relative Standard Deviation (RSD) | | | 0.46% |

Net weight of solution A in the longneck glass bottle: 5.1826 g

Reference time: 2004-1-15 12:30

Background value: 0.006±0.001 MBq

As shown in Table 3, the average concentration of solution A counted for ten times is 48817±223 Bq/g (RSD=0.46%).

(b) Results of measurement and verification for quantitative spray as shown in Table 4:

TABLE 4

Measurement and Verification Results of Solution A for Quantitative Spray

| Stainless plates Nos. | Net Weight (g)$^a$ | Counted Value of Gamma Spectrometer (Bq) | Concentration (Bq/g)$^b$ | Net Weight (mg)$^c$ | Volume (μL)$^d$ |
|---|---|---|---|---|---|
| 1 | 0.0006 | 29.4 ± 2.06 | 49000 | 0.60 | 0.61 |
| 2 | 0.0007 | 36.1 ± 2.60 | 51571 | 0.74 | 0.75 |
| 3 | 0.0008 | 41.0 ± 1.79 | 51250 | 0.84 | 0.85 |
| 4 | 0.0006 | 30.4 ± 2.28 | 50667 | 0.62 | 0.63 |
| 5 | 0.0007 | 34.2 ± 2.13 | 48857 | 0.70 | 0.71 |
| Average | 0.00068 | | 50269 | 0.70 | 0.71 |
| Standard Deviation | 0.00008 | | 1267 | 0.10 | 0.10 |
| Relative Standard Deviation | 12.30% | | 2.52% | 13.65% | 13.65% |

$^a$Net weight (g) = net weight by a scale $^b$concentration (Bq/g) = $\dfrac{\text{counted value of the MCA Gamma Spectrometer (Bq)}}{\text{net weight by a scale (g)}}$ $^c$net weight (g) = $\dfrac{\text{counted value of the MCA Gamma Spectrometer (Bq)}}{\text{average calibrated concentration of solution A (48817 Bq/g)}}$ $^d$volume (μL) = $\dfrac{[\text{counted value of the MCA Gamma Spectrometer (Bq)} \times 1000\ (\mu L/mL)]}{[\text{average calibrated concentration of solution A (48817 Bq/g)} \times \text{density of solution A (0.9881 g/mL)}]}$ As shown in Table 4, the average concentration of solution A is 50269±1267 Bq/g (RSD=2.52%), which is calculated according to five time values measured by dividing MCA gamma spectrometer value (Bq) with the net weight of solution A. Its difference percentage with the calibrated concentration results of solution A (48817 Bq/g) is +2.97%. Therefore, the two results are matched perfectly. The volume of solution A (μL)$^d$ calculated by dividing net weight of solution A (g)$^c$ with density (0.9881 g/mL) demonstrates that the actual volume taken by a micropipette is 0.7±0.1 μL, although a 0.5 μL sample is required.

(c) Results of measurement and verification for stop-flow, as shown in Table 5:

TABLE 5

Results of Measurement And Verification of Solution A for Stop-flow

| Capillary No.s | Volume (μL)$^a$ | Counted Value of the MCA Gamma Spectrometer (Bq)$^b$ | Concentration (Bq/g)$^c$ | Net Weight (mg)$^d$ | Volume (μL)$^e$ | Volume Deviation (%)$^f$ |
|---|---|---|---|---|---|---|
| 1 | 0.350 | 18.1 ± 1.9 | 52504.36 | 0.37 | 0.38 | 7.55 |
| 2 | 0.850 | 41.0 ± 2.9 | 48800.25 | 0.84 | 0.85 | −0.04 |
| 3 | 1.800 | 100.7 ± 5.8 | 56626.75 | 2.06 | 2.09 | 16.00 |
| Average Value | | | 52643.79 | | | 7.84 |
| Standard Deviation | | | 3915.11 | | | 8.02 |

TABLE 5-continued

Results of Measurement And Verification of Solution A for Stop-flow

| Capillary No.s | Volume (μL)$^a$ | Counted Value of the MCA Gamma Spectrometer (Bq)$^b$ | Concentration (Bq/g)$^c$ | Net Weight (mg)$^d$ | Volume (μL)$^e$ | Volume Deviation (%)$^f$ |
|---|---|---|---|---|---|---|
| Relative Standard Deviation | | | 7.44% | | | |

$^a$Volume (μL): measured by the length of solution A in the quantitative capillary
$^b$MCA gamma spectrometer value (Bq): calibrated by the counted value of the MCA gamma spectrometer and the counting geometric factor ($k_{geo}$ = 0.700)

$$^c\text{concentration (Bq/g)} = \frac{[\text{counted value of the MCA gamma spectrometer value (Bq)} \times 1000\ (\mu L/mL)]}{[\text{volume of solution A }(\mu L) \times \text{density of solution A }(0.9881\ g/mL)]}$$

$$^d\text{net weight(g)} = \frac{\text{counted value of the MCA gamma spectrometer value (Bq)}}{\text{average calibrated concentration of solution A }(48817\ Bq/g)}$$

$$^e\text{volume}(\mu L) = \frac{[\text{counted value of the MCA gamma spectrometer value (Bq)} \times 1000\ (\mu L/mL)]}{[\text{average calibrated concentration of solution A }(48817\ Bq/g) \times \text{density of solution A }(0.9881\ g/mL)]}$$

$$^f\text{volume difference (\%)} = \frac{\text{volume}(\mu L)^e - \text{volume}(\mu L)^a}{\text{volume}(\mu L)^a} \times 100\%$$

Figure 5:
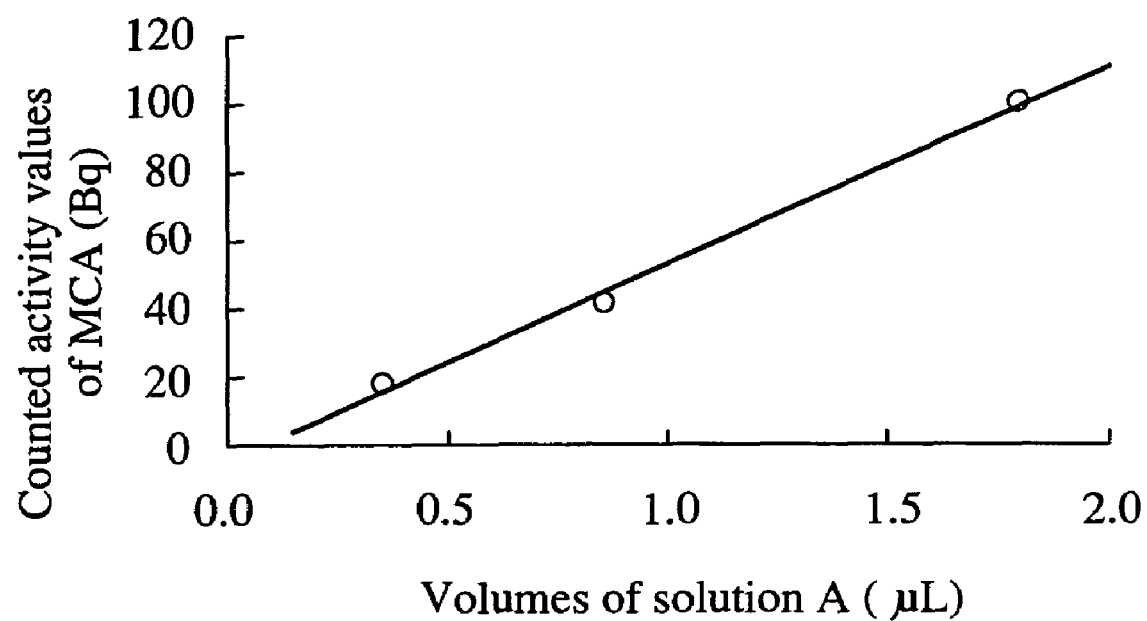
FIG. 5 is a schematic plot view for activity counting and calibration by the MCA gamma spectrometer of the quantitative capillary in example 1 of the present invention.

Although the quantitative capillary is not a point source, fairly well correlation (r=0.9972) shown in the graph of solution A volume and the counted activity value of the MCA gamma spectrometer may demonstrate good quantitative relation between capillaries with different volumes when they are measured by the MCA gamma spectrometer, as shown in FIG. 5. Therefore, the same counting geometric factor $k_{geo}$ may be used for calibration of capillaries with different volumes. As shown in Table 5, the average concentration value of solution A for three times is 52643.79±3915.11 Bq/g, based on the concentration values of solution A calculated by the counted value of the MCA gamma spectrometer divided by the volume of solution A in a capillary. Its difference in percentage with the calibrated concentration results of solution A (48817 Bq/g) is +7.44%. Therefore, the two results are matched perfectly.

(d) Lower limit of volume measurement: lower limit of volume measurement (μL)=[lower limit of detection of the MCA Gamma Spectrometer (MDA, Bq)×1000 μL/mL]/[average calibrated concentration of solution A(48817 Bq/g)×density of solution A (0.9881 g/mL)]=[0.1 Bq×1000 μL/mL]/[148817 Bq/g×0.9881 g/mL]=2.1×10$^{-3}$ μL=2.1 nL Since the solution A has been diluted for about 100 folds, the lower limit of the volume measurement is about 2.1×10$^{-2}$ nL or 21 pL when the original solution is used in the experiment.

Embodiment 2

Provided that the counting efficiency of the MCA gamma spectrometer is 10$_{-5}$, the density of the standard source is 1.05 g/mL, the nuclide concentration of standard source is shown in Table 2, the sample collection time is 60 min, and the counting net value (deducted background counting value) is 50 counts when the reasonable counting time needed for the minimum detectable activity (MDA) of an apparatus activity is considered to be 10000 sec, then ($R_n$-$R_B$) is 5×10$^{-3}$ cps.

TABLE 6

Parameters of Nuclides

| Nuclide | Specific Activity (TBq/g) Sp$_n$ | Atomic Mass (amu) M$_n$ | Concentration (MBq/g) C$_n$' | Concentration (mol/g) C$_n$ |
|---|---|---|---|---|
| Co-60 | 42 | 59.9338 | 0.075 | 2.98 × 10$^{-11}$ |
| Cs-137 | 3.2 | 136.9071 | 0.64 | 1.46 × 10$^{-9}$ |
| Ga-67 | 22000 | 66.9282 | 375 | 2.55 × 10$^{-10}$ |
| I-125 | 640 | 124.9046 | 750 | 9.38 × 10$^{-9}$ |
| I-131 | 4600 | 130.9061 | 750 | 1.25 × 10$^{-9}$ |
| In-111 | 15000 | 110.9051 | 375 | 2.25 × 10$^{-10}$ |
| Mo-99 | 18000 | 98.9077 | 3000 | 1.69 × 10$^{-9}$ |
| Sm-153 | 16000 | 152.9221 | 110 | 4.50 × 10$^{-11}$ |
| Tc-99m | 190000 | 98.9063 | 7500 | 3.99 × 10$^{-10}$ |
| TI-201 | 7900 | 200.9708 | 225 | 1.42 × 10$^{-10}$ |

$V_{total}$, $f_m$, k and k' may be calculated by Formula (10), Formula (12), Formula (13) and Formula (15), as shown in Table 7:

TABLE 7

Results of Calculation

| Nuclide | k (g/cps) | k' (mL/cps) | $V_{total}$ (μL) | $f_m$ (μL/min) |
|---|---|---|---|---|
| Co-60 | 1.3333 | 1.2698 | 6.35 × 10$^{+0}$ | 1.06 × 10$^{-1}$ |
| Cs-137 | 0.1563 | 0.1488 | 7.44 × 10$^{-1}$ | 1.24 × 10$^{-2}$ |
| Ga-67 | 2.67 × 10$^{-4}$ | 2.54 × 10$^{-4}$ | 1.27 × 10$^{-3}$ | 2.12 × 10$^{-5}$ |
| I-125 | 1.33 × 10$^{-4}$ | 1.27 × 10$^{-4}$ | 6.35 × 10$^{-4}$ | 1.06 × 10$^{-5}$ |
| I-131 | 1.33 × 10$^{-4}$ | 1.27 × 10$^{-4}$ | 6.35 × 10$^{-4}$ | 1.06 × 10$^{-5}$ |
| In-111 | 2.67 × 10$^{-4}$ | 2.54 × 10$^{-4}$ | 1.27 × 10$^{-3}$ | 2.12 × 10$^{-5}$ |
| Mo-99 | 3.33 × 10$^{-5}$ | 3.17 × 10$^{-5}$ | 1.59 × 10$^{-4}$ | 2.65 × 10$^{-6}$ |
| Sm-153 | 9.09 × 10$^{-4}$ | 8.66 × 10$^{-4}$ | 4.33 × 10$^{-3}$ | 7.22 × 10$^{-5}$ |
| Tc-99m | 1.33 × 10$^{-5}$ | 1.27 × 10$^{-5}$ | 6.35 × 10$^{-5}$ | 1.06 × 10$^{-6}$ |
| TI-201 | 4.44 × 10$^{-4}$ | 4.23 × 10$^{-4}$ | 2.12 × 10$^{-3}$ | 3.53 × 10$^{-5}$ |

Therefore, according to the $V_{total}$ of Table 7, the effective, selectable lower limit of detection (LLD) for sample single injection or spray may be expected to be about 6 μL (Co-60), about 7 μL (Cs-137), about 1 nl (Ga-67, In-111 and Tl-201), about 0.6 nl (I-125 and I-131), about 0.2 nl (Mo-99) and about 64 pL (Tc-99m) under these assumed conditions.

According to the $f_m$ of Table 7, the effective, selectable lower limit of detection for mobile phase delivery rate may be expected to be about 0.1 μL/min (Co-60), about 12 nl/min (Cs-137), 10~40 pL/min (I-125, I-131, Ga-67, In-111 and Tl-201) and 1~2.6 pL/min (Tc-99m and Mo-99) under these assumed conditions.

Embodiment 3

To decrease the time of measurement and calibration, sample collection time is assumed to be 1 min and other conditions are shown in Example 2 and Table 6, then $V_{total}$, $f_m$, k and k' are calculated by Formula (10), Formula (12), Formula (13) and Formula (15), as shown in Table 8:

TABLE 8

Results of Calculation

| Nuclide | k (g/cps) | k' (mL/cps) | $V_{total}$ (μL) | $f_m$ (μL/min) |
|---|---|---|---|---|
| Co-60 | 1.3333 | 1.2698 | $6.35 \times 10^{+0}$ | $6.35 \times 10^{+0}$ |
| Cs-137 | 0.1563 | 0.1488 | $7.44 \times 10^{-1}$ | $7.44 \times 10^{-1}$ |
| Ga-67 | $2.67 \times 10^{-4}$ | $2.54 \times 10^{-4}$ | $1.27 \times 10^{-3}$ | $1.27 \times 10^{-3}$ |
| I-125 | $1.33 \times 10^{-4}$ | $1.27 \times 10^{-4}$ | $6.35 \times 10^{-4}$ | $6.35 \times 10^{-4}$ |
| I-131 | $1.33 \times 10^{-4}$ | $1.27 \times 10^{-4}$ | $6.35 \times 10^{-4}$ | $6.35 \times 10^{-4}$ |
| In-111 | $2.67 \times 10^{-4}$ | $2.54 \times 10^{-4}$ | $1.27 \times 10^{-3}$ | $1.27 \times 10^{-3}$ |
| Mo-99 | $3.33 \times 10^{-5}$ | $3.17 \times 10^{-5}$ | $1.59 \times 10^{-4}$ | $1.59 \times 10^{-4}$ |
| Sm-153 | $9.09 \times 10^{-4}$ | $8.66 \times 10^{-4}$ | $4.33 \times 10^{-3}$ | $4.33 \times 10^{-3}$ |
| Tc-99m | $1.33 \times 10^{-5}$ | $1.27 \times 10^{-5}$ | $6.35 \times 10^{-5}$ | $6.35 \times 10^{-5}$ |
| Tl-201 | $4.44 \times 10^{-4}$ | $4.23 \times 10^{-4}$ | $2.12 \times 10^{-3}$ | $2.12 \times 10^{-3}$ |

Embodiment 4

Stop-flow mode is used to calibrate the flow rate of the sample in channel of micro fluid chip. The inner diameter of the channel of micro fluid chip (counting loop) is assumed to be 10 μm and the length of the channel is 2 cm, then the total volume of the channel is $\pi \times (5 \times 10^{-6} \text{ meter})^2 \times 0.02 \text{ meter} = 1.57 \times 10^{-3}$ μL. The flow rate of the standard is 0.1 μL/min (i.e. 0.00167 μL/sec), and the other conditions are shown in Example 1 and Table 2, then the movable distance of the standard in one minute is:

$$d = \frac{10^{-10} \text{ m}^3}{\pi \times (5 \times 10^{-6} \text{ m})^2} = 1.273 \text{ m} = 127.3 \text{ cm},$$

or the movable distance per second is 2.12 cm. Under these conditions, the sample collection time (or flow time, $t_{max}$) shall be no more than 0.94 second. Taking nuclide Tc-99m ($V_{min}=V_{total}=6.35 \times 10^{-5}$ μL) for example, the minimum actual measurable time interval (resolution) is:

$$t_{min} = \frac{V_{total}}{f_m} = \frac{6.35 \times 10^{-5} \text{ μL}}{0.1 \text{ μL/min}} = 6.35 \times 10^{-4} \text{ min} = 0.038 \text{ sec.}$$

Then, the moving distance of samples in the channel of micro fluid chip is: $d_{min}=0.038 \text{ sec.} \times 2.12 \text{ cm/sec}=0.8 \text{ mm}$. The other results are shown in Table 9:

TABLE 9

Results of Calculation

| $f_m$ (μL/min) | $f_m'$ (cm/sec) | $t_{max}$ (sec) | $t_{min}$ (sec) | $d_{min}$ (mm) |
|---|---|---|---|---|
| 0.1 | 2.12 | 0.94 | 0.038 | 0.8 |
| 0.01 | 0.212 | 9.4 | 0.381 | 0.8 |
| 0.001 | 0.0212 | 94 | 3.81 | 0.8 |

The following claims are intended to define the reasonable protective scope of the invention. It shall be understood by those skilled in the art that apparent improvements based on the disclosures of the invention are also within the scope of the invention.

What is claimed is:

1. A method for measuring the sample injection volume and the mobile phase delivery rate in an ultra micro-scale liquid phase delivery system, comprising the following steps:

(1) selecting a suitable radiochemical substance as a nuclide of the sample to prepare a source solution, based on the micro grade of the volume and the flow rate to be measured;

(2) collecting the source solution for a time period t and measuring a the counting rate ($R_n$) of the collected source solution by a radio activity counting apparatus; and (3) calculating the volume and the delivery rate of the collected source solution by Formula A and Formula B;

$$V_{total} = \frac{R_n - R_B}{C_n \times M_n \times Sp_n \times Eff_n} \quad \text{Formula A}$$

$$f_m = \frac{R_n - R_B}{C_n \times M_n \times Sp_n \times Eff_n \times t} \quad \text{Formula B}$$

wherein, $V_{total}$ is the sample volume, $f_m$ is the delivery rate, the counting rate ($R_n$) is obtained from actual counting of the radioactivity counting apparatus and modified by the half-life period calibration, $R_B$ is the background counting rate which is obtained from actual counting of the radioactivity counting apparatus for an empty vial, $C_n$ is the concentration of the source solution, $M_n$ is the atomic mass of the nuclide, $Sp_n$ is the specific activity of the nuclide, $Eff_n$ is the counting efficiency of the nuclide which is obtained by standard source calibration of the radio activity counting apparatus, and t is the collection time.

2. A method for measuring and calibrating the sample injection volume and the mobile phase delivery rate in an ultra micro-scale liquid phase delivery system, comprising the following steps:

(1) selecting a suitable radiochemical substance as a nuclide of the sample to prepare a source solution, based on the micro grade of the volume and the flow rate to be measured and calibrated;

(2) collecting the source solution with a predetermined flow rate ($f_m'$) for a time period of t and calculating the predetermined volume ($V_{total}'$) of the collected source solution;

(3) measuring a counting rate ($R_n$) of the collected source solution by a radio activity counting apparatus;

(4) calculating the sample volume and the delivery rate of the collected source solution by Formula A and Formula B:

$$V_{total} = \frac{R_n - R_B}{C_n \times M_n \times Sp_n \times Eff_n} \qquad \text{Formula A}$$

$$f_m = \frac{R_n - R_B}{C_n \times M_n \times Sp_n \times Eff_n \times t} \qquad \text{Formula B}$$

wherein, $V_{total}$ is the actual volume, $f_m$ is the actual flow rate, the counting rate ($R_n$) of the source solution is obtained from actual counting of the radioactivity counting apparatus and modified by the half-life period calibration, $R_B$ is the background counting rate which is obtained from actual counting of the radioactivity counting apparatus for an empty vial, $C_n$ is the concentration of the source solution, $M_n$ is the atomic mass of the nuclide, $Sp_n$ is the specific activity of the nuclide, $Eff_n$ is the counting efficiency of the nuclide which is obtained by standard source calibration of the radioactivity counting apparatus, and t is the collection time; and (5) calibrating the predetermined volume ($V_{total}'$) and the predetermined flow rate ($f_m'$) according to the actual volume ($V_{total}$) and the actual flow rate of the source solution.

3. The method according to claim 1, wherein the micro-scale volume grade is between μL and pL, and the micro-scale flow rate grade is between μL/min and pL/min or is mm/min.

4. The method according to claim 1, wherein the source solution is collected by fractional collection, stop-flow, or quantitative spray.

5. The method according to claim 1, wherein the nuclide is that applicable for direct counting by the radioactivity counting apparatus.

6. The method according to claim 5, wherein the nuclide is that with gamma decay or electron capture decay property.

7. The method according to claim 5, wherein the radioactivity counting apparatus comprises an MCA gamma spectrometer, a gas proportional counter, a dose calibrator, or an ion chamber.

8. The method according to claim 1, wherein the nuclide is that without gamma decay or electron capture decay property and must be mixed with a cocktail scintillator, and then calibrated by the radioactivity counting apparatus.

9. The method according to claim 8, wherein the nuclide is a pure beta decay nuclide.

10. The method according to claim 8, wherein the radioactivity counting apparatus is a liquid scintillation analyzer.

11. The method according to claim 1, which is applicable for measuring the sample injection volume, the spray volume, the dipper adhesive volume, or the delivery rate in the mobile phase of the ultra-microscale liquid phase delivery system.

12. The method according to claim 2, wherein the micro-scale volume grade is between μL and pL, and the micro-scale flow rate grade is between μL/min and pL/min or is mm/min.

13. The method according to claim 2, wherein the source solution is collected by fractional collection, stop-flow, or quantitative spray.

14. The method according to claim 2, wherein the nuclide is that applicable for direct counting by the radioactivity counting apparatus.

15. The method according to claim 14, wherein the nuclide is that with gamma decay or electron capture decay property.

16. The method according to claim 14, wherein the radioactivity counting apparatus comprises an MCA gamma spectrometer, a gas proportional counter, a dose calibrator, or an ion chamber.

17. The method according to claim 2, wherein the nuclide is that without gamma decay or electron capture decay property and must be mixed with a cocktail scintillator, and then calibrated by the radioactivity counting apparatus.

18. The method according to claim 17, wherein the nuclide is a pure beta decay nuclide.

19. The method according to claim 17, wherein the radioactivity counting apparatus is a liquid scintillation analyzer.

20. The method according to claim 2, which is applicable for measuring the sample injection volume, the spray volume, the dipper adhesive volume, or the delivery rate in the mobile phase of the ultra-microscale liquid phase delivery system.

* * * * *